United States Patent [19]
Arrhénius-Nyberg et al.

[11] Patent Number: 5,994,303
[45] Date of Patent: *Nov. 30, 1999

[54] USE OF INSULIN AND IGF-I

[75] Inventors: Vibeke Arrhénius-Nyberg, Järfälla; Kjell Malmlöf, Solna; Anna Skottner, Ekerö, all of Sweden

[73] Assignee: Chiron Corporation, Emeryville, Calif.

[ * ] Notice: This patent is subject to a terminal disclaimer.

[21] Appl. No.: 09/002,703

[22] Filed: Jan. 5, 1998

Related U.S. Application Data

[63] Continuation of application No. 08/750,735, Dec. 18, 1996, Pat. No. 5,756,463.

[30] Foreign Application Priority Data

Jul. 1, 1994 [SE] Sweden ................................ 9402331

[51] Int. Cl.$^6$ ............................ A61K 38/00; A61K 31/40

[52] U.S. Cl. .................................... 514/12; 514/3; 514/4; 514/21; 530/303; 530/306

[58] Field of Search .................................... 514/4, 12, 21, 514/3; 530/303, 306

[56] References Cited

U.S. PATENT DOCUMENTS

| | | | |
|---|---|---|---|
| 4,988,675 | 1/1991 | Froesch et al. | 514/4 |
| 5,091,173 | 2/1992 | Buultjens et al. | 514/3 |
| 5,128,320 | 7/1992 | Hahn et al. | |
| 5,434,134 | 7/1995 | Gluckman et al. | |

FOREIGN PATENT DOCUMENTS

| | | |
|---|---|---|
| 0 501 937 A1 | 1/1992 | European Pat. Off. |
| WO 91/10348 | 7/1991 | WIPO |
| WO 92/03154 | 3/1992 | WIPO |
| WO 96/01124 | 1/1996 | WIPO |
| WO 96/01125 | 1/1996 | WIPO |
| WO 96/02270 A1 | 2/1996 | WIPO |

*Primary Examiner*—Leon B. Lankford, Jr.
*Assistant Examiner*—Christopher R. Tate
*Attorney, Agent, or Firm*—W. Murray Spruill; Joseph H. Guth; Robert P. Blackburn

[57] ABSTRACT

A combination of insulin and an insulin-like growth factor I (IGF-I) as used in the manufacture of a medicament for counteracting a decrease in nitrogen balance and for counteracting a decrease in protein synthesis. The medicament can be used for the treatment of catabolism which is a protein catabolism due to glucocorticoid excess.

20 Claims, 4 Drawing Sheets

USE OF INSULIN AND IGF-I

CROSS-REFERENCE TO RELATED APPLICATION

This is a continuation of U.S. patent application Ser. No. 08/750,735, filed Dec. 18, 1996, now U.S. Pat. No. 5,756,463, herein incorporated by reference in its entirety.

The present invention relates to the use of a combination of insulin and Insulin-like Growth Factor (IGF-I) for the manufacture of a medicament for counteracting a decrease in nitrogen balance and for counteracting a decrease in protein synthesis. The medicament can be used in the treatment of catabolism, to increase in body protein, and in protein synthesis.

The invention also relates to a method for counteracting a decrease in nitrogen balance and counteracting a decrease in protein synthesis.

INTRODUCTION

It is well recognised that the protein catabolism normally observed during different states of critical illness is influenced by hormones such as glucagon, catecholamines and glucocorticoids (Alberti et al. 1980; Smith & Williamson 1983; Bessey & Lowe 1993).

Glucocorticoids have been associated with a decrease in protein synthesis and an increase in protein catabolism (Kayall et al. 1978; Simmons et al. 1984) and also with an increase in the excretion of nitrogen in urine (Long et al. 1940; Sapir et al. 1977). These effects are probably partly mediated via a decrease in growth hormone secretion (Trainer et al. 1991) but could also be the result of direct action of glucocorticoids on the tissue level (Baron et al. 1992), therewith also interfering with the local production of insulin like growth factor I (McCarthy et al. 1990) and antagonising the action of insulin (Horber et al. 1991). Because of the strong catabolic effects exerted by glucocorticoids these substances have either been used alone (Tomas et al. 1992) or in combination with other catabolic hormones (Bessey & Lowe 1993) to produce models in which the effects of agents that have an anticipated potential of reversing protein catabolism can be studied. Previous studies on rats have demonstrated that the catabolic action of glucocorticoid analogues, such as dexamethasone, can be counteracted by recombinant human insulin-like growth factor I (rhIGF-I) and its analogues (Tomas et al. 1992). The effect of recombinant human growth hormone (rhGH), however, appears more variable and some studies carried out on growing rats have shown that this hormone is inefficient in reversing glucocorticoid induced catabolism (Örtoft et al 1993), whereas studies in humans have pointed to positive effects (Horber & Hammond 1990).

Not only rhIGF-I and rhGH but also insulin have individually been shown to ameliorate protein catabolism (Woolfson et al. 1979).

In WO 9110348 there is claimed a method for restoring normal growth, weight gain and lean body mass of mammal with glucocorticoid excess by administering IGF-I.

The potency of the combination of GH and IGF-I in terms of improving nitrogen balance is suggested by Clemmons et al, Horm Res., 40 (1–3), 62–67, 1993 and Genn et al, Biochem. Arch., 5(1), 53–59, 1989 discloses the anabolic effect of insulin and IGF-II.

Fuller S. J. et al, Biochem Soc Trans 19(3), 1991, p. 277S describes the stimulation of cardiac protein synthesis after treatment with insulin and IGF. The experiments have been performed in vitro with freshly isolated cardiac myocytes.

Umpleby A. M. et al Europ J Clin Invenst 24(5), 1994, p. 337–344, reports on effects on protein metabolismus after treatment with insulin and IGF on dogs which have been starved overnight. No medicaments for counteracting decrease in nitrogen balance have been disclosed in these documents.

THE INVENTION

The invention thus relates to the use of a combination of insulin and IGF-I in the manufacture of a medicament for counteracting a decrease in nitrogen balance and for counteracting a decrease in protein synthesis. The invention can be applied in the treatment of protein catabolism caused by glucocortoid excess and the medicament can be used for patients that suffer from cardiac diseases.

The ratio of IGF-I and insulin in the medicament could be in a range of 30:1 to 2:1 based on molecular weight, preferably in a range of less than 10:1 and more preferably in a range of less than 8:1.

IGF-I is preferably administered in a dose of 20 to 500 microgram/kg and insulin is preferably administered in a dose of 10 to 100 microgram/kg.

The invention also relates to the use of a combination of insulin and IGF-I in the manufacture of a medicament for the treatment of patients having high serum levels of IGF-I binding protein 1 (IGFBP1) or other low molecular weight BPs, such as malnourished patients, insulin resistant patients or patients with liver diseases or patients suffering from cardiac diseases.

The invention also relates to a method for counteracting a decrease in nitrogen balance and for counteracting a decrease in protein synthesis by administration of a combination of insulin and IGF-I and for the treatment of protein catabolism due to glucocortoid excess, by the administration of a combination of insulin and IGF-I.

The combination of insulin and IGF-I results in a surprising synergistic effect.

DETAILED DESCRIPTION OF THE DRAWINGS

Figure 1A:
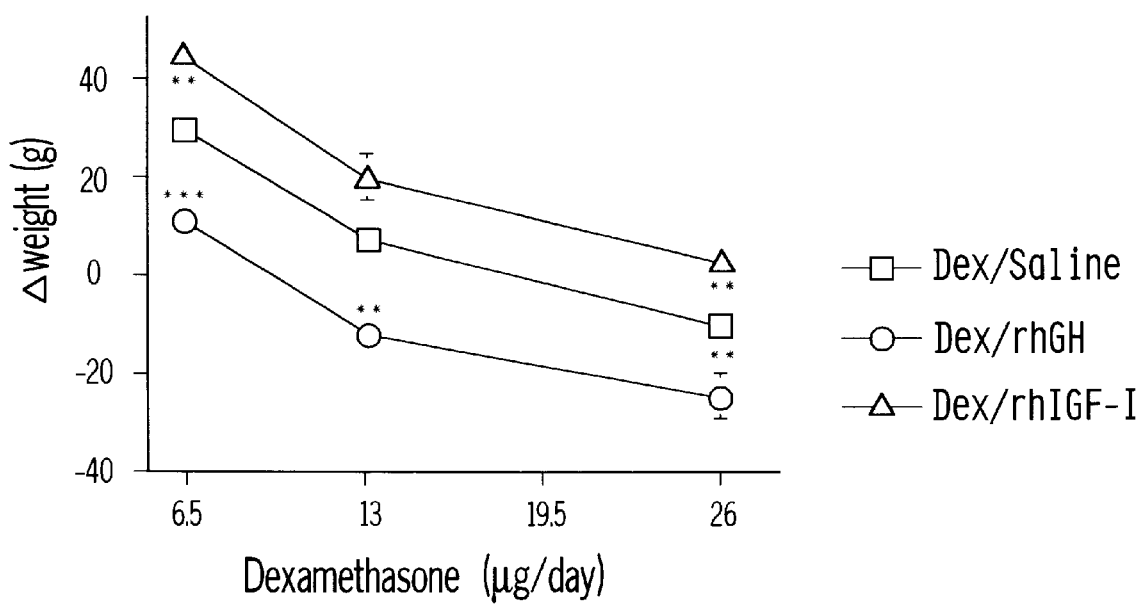
Figure 1B:
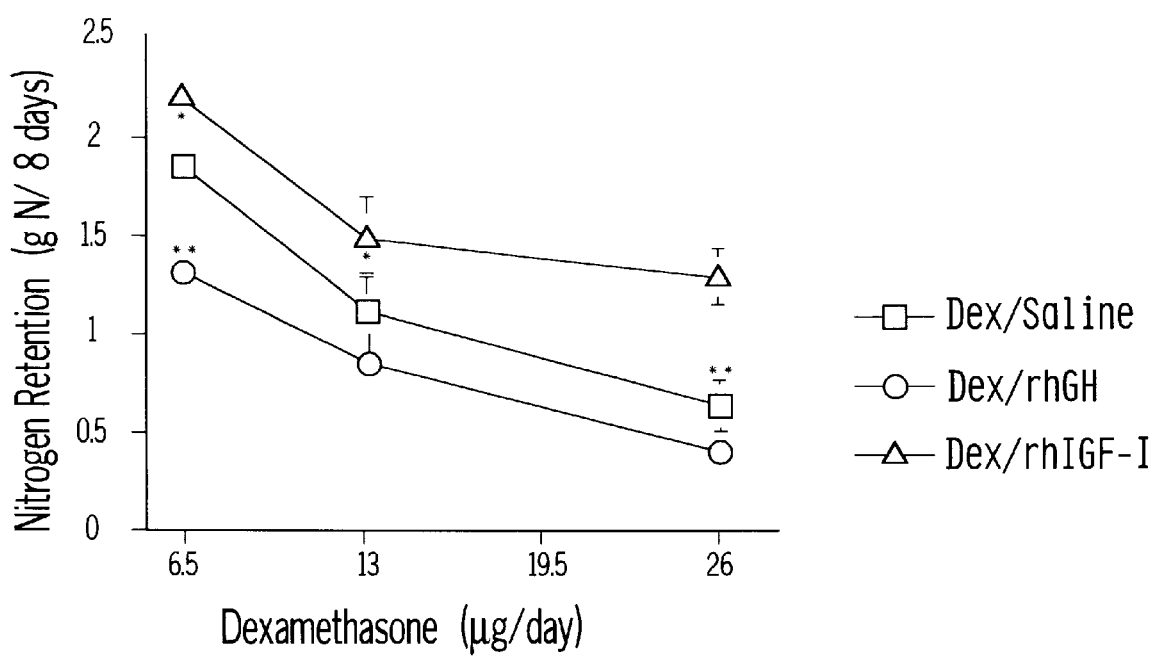

The following figures are illustrating the invention:

FIGS. 1a and 1b: Mean change in body weight and cumulative nitrogen retention (example 1)

Figure 2A:
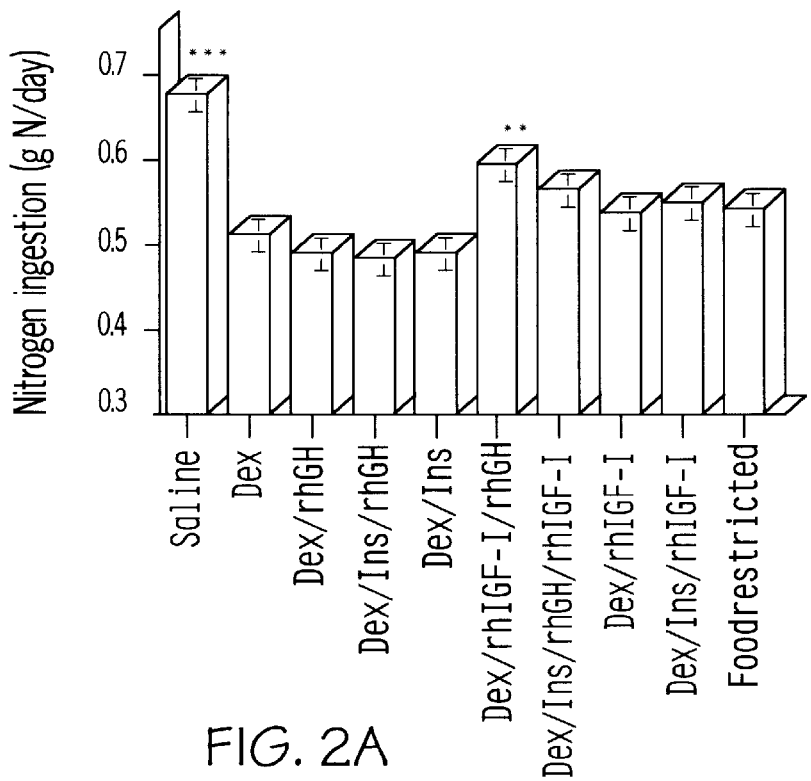
Figure 2B:
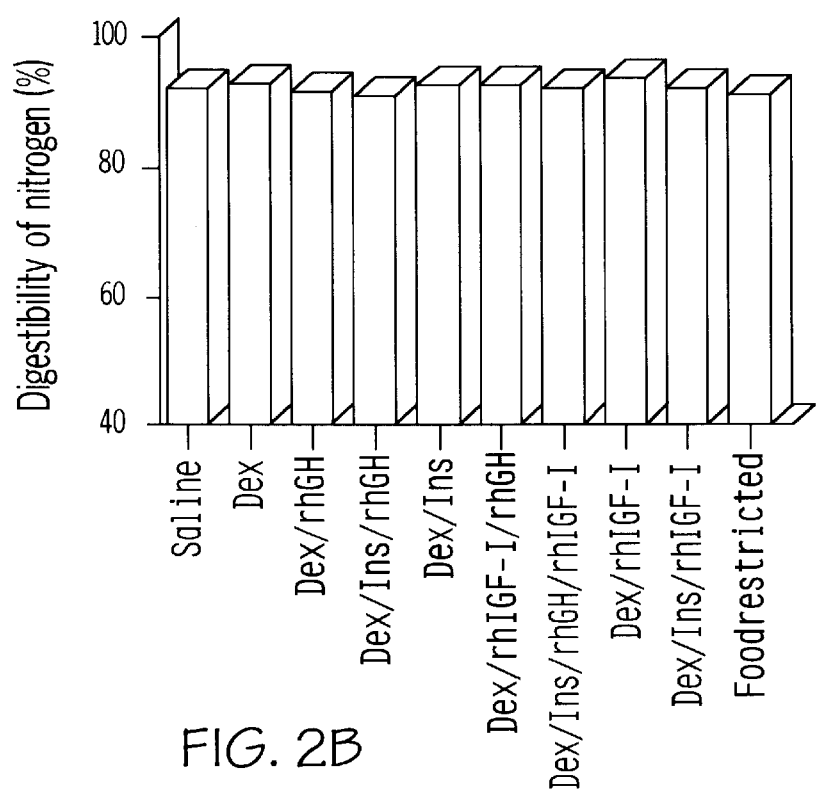

FIGS. 2a and 2b: Mean daily ingestion and digestability of dietary nitrogen (example 2)

Figure 3A:
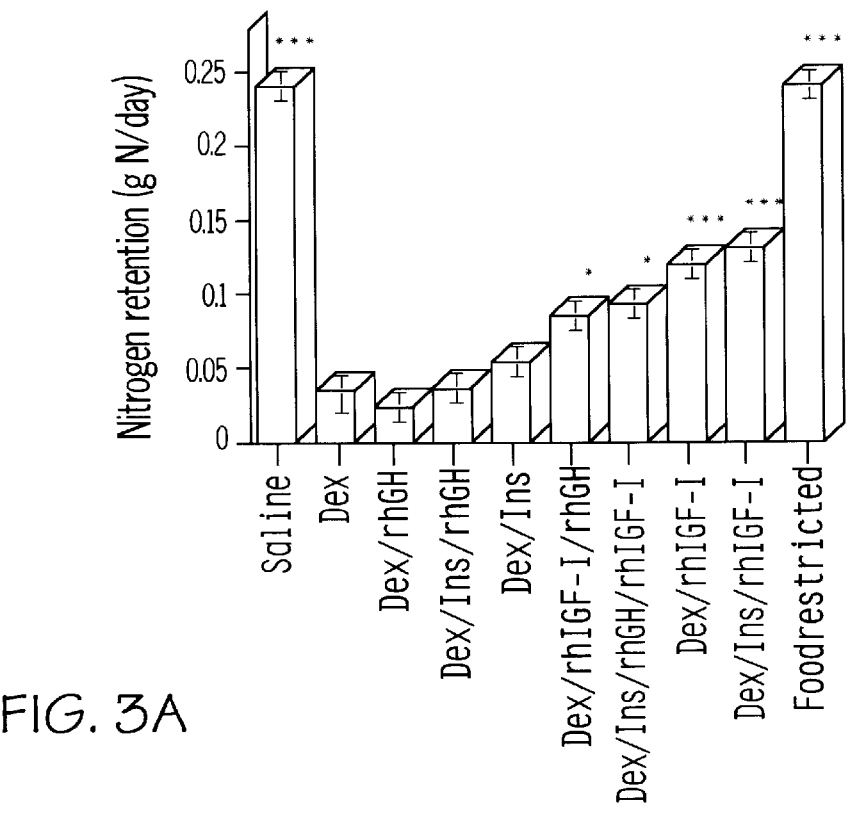
Figure 3B:
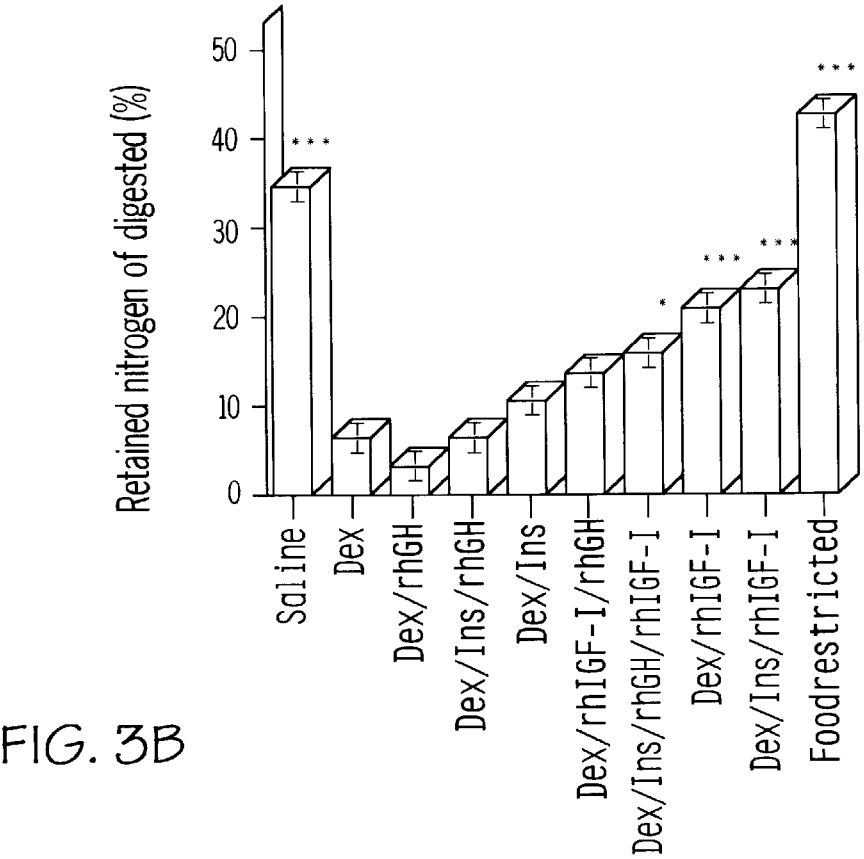

FIGS. 3a and 3b: Mean daily retention and relative retention of nitrogen (example 2)

Figure 4:
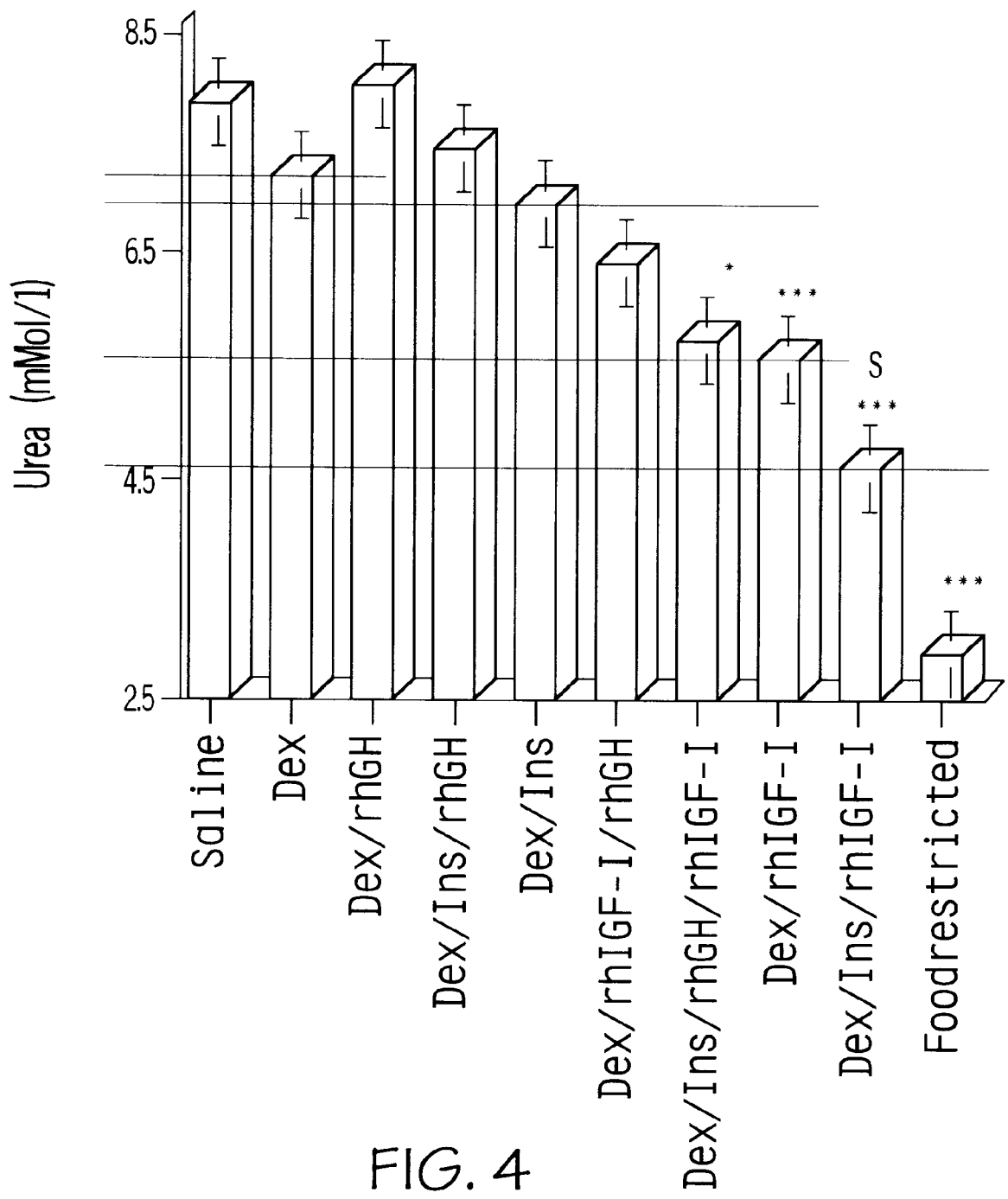

FIG. 4: Mean concentration of serum urea (example 2).

EXAMPLES

MATERIALS AND METHODS

Experimental procedures

Surgery

On day zero the rats were anaesthetized intraperitoneally with 0.4 ml per 100 g body weight of a mixture of Rompun (20 mg·ml$^{-1}$), Ketalar (50 mg·ml$^{-1}$) and Saline (0.9%) in 1:2:3 volume proportions. The hair on the back of the rats was shaved off and the exposed skin carefully washed with 0.05% chlorhexidine (Pharmacia, Stockholm, Sweden) and 0.4% jodopax (Mölnlycke, Göteborg, Sweden), both being diluted in 70% alcohol.

Two mutually parallel incisions, each of 15 mm in length, were then made along the dorsal midline. The incisions penetrated the epidermis, dermis and subcutaneous muscle but left the deep fascia intact. Two subcutaneous pockets were made on both sides of the incisions by separating the subcutaneous muscle from the deep fascia. One (Exp. I) or two (Exp. 2) mini-pumps were implanted in each pocket. The wounds were closed with sutures 4-0 Johnson & Johnson).

Infusion of hormones

Osmotic mini-pumps (Alzet 2001, Alza Corporation, Palo Alto, USA) releasing 1 $\mu l \cdot h^{-1}$ for 8 days were used for continuous delivery of hormones and Dex to the animals. The pumps were filled to a volume of 0.22 ml with solutions of rhGH (14.4 mg·ml$^{-1}$, Genotropin®, Pharmacia), rhIGF-I (20 mg·ml$^{-1}$, Igef®, Pharmacia, Kabi Peptide Hormones, Stockholm, Sweden), insulin (1.57 mg/ml, Actrapid®, Novo, Copenhagen, Denmark), Dex (1.04 mg·ml$^{-1}$, Decadron, Merck Sharp & Dohme International, Rathway, USA) or Saline (0.9%). Two (Example 1) or four (Example 2) pumps combined as described above were implanted in each rat. Implantation of the pumps was performed under strictly aseptic conditions.

Collection of urine and faeces

Total feed intake was registered throughout the full 8 day experimental period. Urine and faeces were collected daily, pooled and kept at −20° C. until analysed. Excreta was collected by housing the animals in individual metabolism cages that were specially designed for the separation of urine and faeces. In order to inhibit urease-activity in the urine, 1 ml of 5% sulphuric acid was pipetted every morning in the collection vessels. The 24 hour collections of urine were pooled individually for each treatment period and immediately frozen after the collection. Similarly, the samples of faeces were also pooled individually for each treatment period and kept frozen (−20° C.) until analysis.

Sampling of blood

Blood samples were taken on day zero and on the last day of the experiment. During anaesthesia, blood was withdrawn quickly from the orbital plexus by using a glass capillary. On each sampling occasion 0.75 ml blood was taken 5 from each animal. One third (0.25 ml) of the blood sample was collected in a microtainer tube containing EDTA (Beckton and Dickinson) for analysis of glucose. Serum was prepared from the remaining blood sample (0.5 ml) in accordance with standard methods and analysed for urea.

Analyses

Urea in serum was determined spectrophotometrically by using the Urea UV Uni-Kit II (Roche) with an autoanalyzer (Cobas Mira, Roche Co, Basel, Switzerland). Urea values were expressed in mmol/l. The total nitrogen content in urine was determined with the aid of the Antek Pyro-Chemilumicence Nitrogen System. The apparatus used comprised the Antek 7000N nitrogen analyser with Liquid Auto Sampler 736-2 and a pyrolysis tube with a ceramic liner (Antek Instruments Inc., Houston, Tex., U.S.A.). The frozen urinary samples were thawed and diluted 1:100 with 0.1 M HCl and then analysed. The urinary nitrogen values were then calculated as mg nitrogen excreted.

Total nitrogen in faeces was determined by an established Kjeldahl method (Kjeltec System, Tecator AB, Hälsingborg, Sweden). The frozen faecal samples were thawed and dried in an oven at 60° C. overnight. The weight of the dried sample was noted and the sample then ground. 0.20 g of the milled faecal sample was mixed in a Kjeldahl digestion tube with 10.0 ml of concentrated sulphuric acid. 2.0 ml of a 30% solution of $H_2O_2$ (30% Perhydrol, Merck, Darmstadt, Germany) was added and mixed carefully. One catalyst tablet (Kjeltabs C A, Thompson & Capper, Runcom, Cheshire, UK) was added to each sample. The mixture was digested at 380° C. for at least one hour or until complete bleaching of the sample was achieved. The nitrogen content of this solution was determined after alkalinization by steam distillation of the ammonia and automated titration of the distillate. The faecal nitrogen values were calculated as mg nitrogen excreted.

Statistics

Data were subjected to a one-way analysis of variance in which the effect of treatment was considered the prime source of variation. Calculations were executed by the GLM procedure of the SAS program (SAS 1985). Unless otherwise stated the SE specifications used represent the pooled standard error derived from the analyses of variance. Values were considered to be significantly different with P values less than 0.05.

EXAMPLE I

Male Sprague-Dawley rats each weighing approximately 200 g (B&K Universal AB, Sollentuna, Sweden) were fitted with 2 osmotic mini-pumps, subcutaneously. Three main groups of 18 rats each received pumps which delivered dexamethasone (Dex) at either one of the following rates 26 $\mu d \cdot day^{-1}$, 13 $\mu d \cdot day^{-1}$ or 6.5 $\mu d \cdot day^{-1}$, respectively. Each of these three Dex-dose groups was further divided into three groups each containing 6 rats. The animals of these groups were fitted with another mini-pump providing subcutaneous infusions of either saline, rhGH at a rate of 360 $\mu d \cdot day^{-1}$ or rhIGF-I at a rate of 500 $\mu d \cdot day^{-1}$. The rats were placed individually in metabolic cages which allowed free access to water and a ground feed comprising 222 g crude protein/kg and 3.6 Mcal/kg of metabolizable energy. The rats were subjected to a light/dark cycle of 12/12 hours. Dex, saline and peptides were infused and excreta collected over an 8 days period. The data in FIG. 1 represents mean values of six observations made with pooled SEM. Significant differences between Dex/saline and other groups are shown, * ($p<0.05$).  ($p<0.001$), * ($p<0.001$)

Results

See FIG. 1

Body weight gain showed a general decrease with increased Dex dose. At every Dex dose infusion of rhIGF-I was associated with significantly ($p<0.05$) higher weight gain in comparison with saline, whereas hGH had the opposite effect ($p<0.05$). At the medium and high infusion dose even negative values for body weight gain were registered among animals administered with rhGH. At the highest Dex dose, animals to which only saline was administered also lost weight. The positive effect on body weight gain afforded by rhIGF was also seen in the corresponding nitrogen balances. Thus, the retention of nitrogen was also significantly ($p<0.05$) higher during rhIGF-I treatment in comparison with any of the others.

EXAMPLE 2

Male Sprague-Dawley rats (B&K Universal AB, Sollentuna, Sweden) weighing approximately 200 g were fitted with 4 osmotic mini-pumps allowing infusions of 9 unique combinations of saline (0.9 NaCl, 25 $\mu l$, day-1), Dex (dexamethasone, 26 $\mu d \cdot day^{-1}$), insulin (39 $\mu g\ day^{-1}$), rhGH (360 $\mu g\ day^{-1}$) and rhIGF-I (500 $\mu g \cdot day^{-1}$), in accordance with Table I. Groups, each containing 6–14 rats, received the same infusion regimen Dex reduced feed intake by approximately 20% and therefore an additional group of animals given this plane of nutrition was later enrolled in the study.

All rats were placed individually in metabolic cages with free access to water and a ground feed. The diet comprised 222 g crude protein·kg$^{-1}$ and 3.6 Mcal·kg$^{-1}$ of metabolizable energy. The rats were subjected to a 12/12 h light-dark cycle. Infusion of peptides, and quantitative collection of urine and faeces were maintained for 8 days.

TABLE 1

Experimental scheme

| Group | Pump 1 | Pump 2 | Pump 3 | Pump 4 |
|---|---|---|---|---|
| 1 | saline | saline | saline | saline |
| 2 | dexamethasone | saline | saline | saline |
| 3 | dexamethasone | rhGH | saline | saline |
| 4 | dexamethasone | rhIGF-I | saline | saline |
| 5 | dexamethasone | rhIGF-I | rhGH | saline |
| 6 | dexamethasone | insulin | saline | saline |
| 7 | dexamethasone | insulin | rhGH | saline |
| 8 | dexamethasone | insulin | rhGH | rhIGF-I |
| 9 | dexamethasone | insulin | rhIGF-I | saline |
| 10 | none | none | none | none |

*The rats in group 10 were fed 120 g which was the average feed consumption of rats in groups 1–8, and 80% of the consumption from rats receiving infusions of saline alone.

Results

See FIGS. 2, 3, and 4

Administration of Dex generally decreased feed intake. It appeared also as if infusions comprising rhIGF-I, either alone or in combination with other peptides, slightly stimulated feed consumption. The digestion of nitrogen was strikingly similar between treatments and no differences could be seen (See FIG. 2).

The data in FIG. 2 represents mean values of 6–14 observations together with error bars (pooled SE). ($p<0.01$) *($p<0.001$) significant differences between the Dex group and other groups.

Administration of Dex/saline reduced the nitrogen retention, calculated both in absolute terms and in relative terms as retained N/digested N (See FIG. 3). Thus, the relative nitrogen retention within the two groups without Dex, the feed-restricted group and the group treated with saline alone was 48.4% SE 3.5) and 38.7% (SE 4.5), respectively. This decreased to 7.2% (SE 3.5) hen Dex/saline was administered, this decrease being highly significant ($P<0.0001$). Corresponding figures when peptides were infused together with Dex were in the following ascending order: rhGH 3.8% (SE 3.5), insulin/rhGH 7.8% (SE 3.5), insulin 11.9% (SE 3.5), rhIGF-I/rhGH 15.3% (SE 2.9), insulin/rhGH/rhIGF-I 17.5% (SE 2.9), rhIGF-I 23.0% (SE 2.9), insulin/rhIGF-I 25.7% (SE 2.9). The difference between Dex/saline and Dex/peptides was statistically significant ($p<0.02$) from insulin/rhGH/rhIGF-I 17.5% (SE 2.9) and onwards in the series above. The effect of admixing insulin with the rhIGF-I infusion regimen was not statistically different from that of rhIGF-I alone.

The data in FIG. 3 represents mean values of 6–14 observations together with error bars (pooled SE). *($p<0.05$). ***($p<0.001$). significant differences between the Dex group and other groups.

In general there was a close inverse relationship between nitrogen balance and circulating levels of urea registered on the last day of experiment (See FIG. 4). Moreover, the combined infusion of insulin and rhIGF-I in the Dex treated groups, produced a significantly ($p<0.03$) lower urea level than did rhIGF-I alone.

The data in FIG. 4 represents mean values of 6–14 observations together with error bars (pooled SE). *($p<0.05$). ***($p<0.001$). significant differences between the Dex group and other groups. S($p<0.05$) significant differences between the Dex/rhIGF-I group and the Dex/Ins/rhIGF-I group.

DISCUSSION

In the present study the administration of dexamethasone to rats was found to decrease the nitrogen balance dramatically. Our results show that this was not due to the relatively small decrease in feed intake caused by dexamethasone, since feed restriction without dexamethasone had a similar effect on nitrogen balance as could be seen among saline infused animals with no feed restriction. In this connection it is also interesting to note that the digestibility of nitrogen was strikingly similar among all treatments. Taken together these results suggest that the proportion of nitrogen excreted in the urine of the amount absorbed increased with dexamethasone and that this was the main cause of the major decrease in nitrogen balance registered. This effect of glucocorticoids is well established (Long et al. 1940; Sapir et al. 1977).

In the present study rhGH was given in a dose which was about six times higher than what is necessary to stimulate growth significantly in dwarf rats (Skottner et al. 1989). Despite this, rhGH was not found to counteract the nitrogen wasting induced by dexamethasone. This is in agreement with previous studies on rats (Örtoft et al 1993), but in contrast to what has been found in humans (Horber & Hammond 1990). Horber & Hammond (1990) found that hGH could significantly attenuate the decrease in nitrogen balance produced by glucocorticoid treatment. It cannot be excluded that these discrepancies in results are due to species differences with regard to receptor specificity and binding kinetics of hGH (Amit et al. 1993), combined with fundamental differences in glucocorticoid physiology that is known to exist. In rats the principle glucocorticoid is corticosterone and not cortisol as in man.

(Shimizu et al. 1983).

In the present study it was observed that rhIGF-I in contrast to rhGH, decreased significantly the wasting of nitrogen induced by dexamethasone. This confirms previous results obtained with rats (Tomas et al., 1992). When insulin was admixed with the infusion of rhIGF-I, this produced a higher nitrogen balance and lower circulating levels of urea as compared with the infusion of rhIGF-I alone. It is suggested that if insulin can potentiate the anticatabolic effect of rhIGF-I, as indicated by our urea data, this might possibly be due to decreased levels in one of IGF-I's binding proteins, IGFBP-I (Brismar et al 1991).

In the present study no measurements were taken of IGFBP, although studies on the rats show that dexamethasone increases IGFBP-I in vivo (Luo & Murphy 1990). The reason why this has not always been found in humans (Miell et al 1992) is probably due to the dominant suppressive role of insulin on IGFBP-I production (Brismar et al 1991, Conover et al. 1993).

Finally, it could be concluded that rhIGF-I, but not rhGH, counteract the protein catabolism induced by glucocorticoids, and that this action appears potentiated by insulin.

CONCLUSION

Administration of glucocorticoids is associated with a decreased nitrogen balance. The main aim of the present study was to elucidate whether this could be counteracted by certain peptide hormones. Initially, the effects of recombinantly manufactured human growth hormone (rhGH, 360 $\mu$g·day$^{-1}$) and insulin-like growth factor I (rhIGF-I, 500 $\mu$g·day$^{-1}$) were compared with saline at three doses of dexamethasone (Dex; 26, 13, or 6.5 $\mu$g·day$^{-1}$). At all doses of Dex, body weight gain measured after 8 days of study was significantly ($p<0.05$) increased by rhIGF-I compared with saline, whereas rhGH had the opposite effect. Nitrogen retention followed the same pattern. In a second experiment, groups of 6–14 animals were administered Dex (26 $\mu$g·day$^{-1}$) together with either saline, rhGH (360 $\mu$g·day$^{-1}$), rhIGF-I (500 $\mu$g·day$^{-1}$) or insulin (39 $\mu$g·day$^{-1}$), for 8 days. The peptides were also administered in a double or triple combination. In addition, one group was given saline alone, without Dex. This latter administration produced a nitrogen retention (retained N/digested N×100) of 38.7% (SE 4.5), which was decreased ($p<0.0001$) to 7.2% (SE 3.46) when Dex without peptide was administered. This figure, however, was increased significantly ($p<0.02$) up to 17.5, 23.0 and 25.7% (SE 2.92) if Dex was combined with insulin/rhGH/rhIGF-I, rhIGF-I or insulin/rhIGF-I, respectively. In the doses used, insulin or GH alone were without effect as well as rhGH combined with either rhIGF-I or insulin. Although the nitrogen retentions associated with insulin/rhIGF-I and rhIGF-I alone were not found to be significantly different, the former infusion regimen produced a significantly ($p<0.02$) lower plasma urea level when compared with rhIGF-I alone. It is concluded that in the rat, rhIGF-I alone, but not rhGH, has a potential to counteract the decrease in nitrogen balance induced by glucocorticoids, and that additions of insulin might further potentiate the effect of rhIGF-I.

REFERENCES

Alberti K G M M, Phil D, Batstone G F, Foster K J, Johnston D G. Relative role of various hormones in mediating the metabolic response to injury. J Parent Ent Nutr 1980; 4: 141–146.

Amit T, Hochberg Z, Waters M J and Barkey R J. Growth hormone- and prolactin-binding proteins in mamalian serum. Endocrinology 1992; 131: 1739–1803.

Baron J, Huang Z, Oerter K E, Bacher J D and Cutler Jr, G B. Dexamethasone acts locally to inhibit longitudinal bone growth in rabbits. Am J Physiol 1992; 263: E489–E492.

Bessey P Q and Lowe K A. Early hormonal changes affect the catabolic response to trauma. Ann Surg 1993; 218: 476–491.

Brismar K, Grill V, Efendic S and Hall K. The insulin like growth factor binding protein-I in low and high insulin responders before during after dexamethasone treatment. Metabolism 1991; 40: 728–732.

Conover C A, Divertie G D and Lee P D K. Cortisol increases plasma insulin-like growth factor binding protein-1 in humans. Acta Endocrinol, 1993; 128: 140–143.

Horber F F and Haymond M. W. Human growth hormone prevents the protein catabolic side effects of prednisone in humans. J Clin Invest 1990; 86: 265–272.

Horber F F, Marsh H M and Haymond M W. Differential effects of Prednisone and growth hormone on fuel metabolism and insulin antagonism in humans. Diabetes 1991; 40: 141–149.

Kayali A G, Young V R and Goodman A M. Sensitivity of myofibrillar proteins to glucocorticoid-induced muscle proteoloysis. Am J Physiol 1987; 252: E621–E626.

Long C H N, Katzin B and Fry E G. The adrenal cortex and carbohydrate metabolism. Endocrinology 1940; 26: 309–344.

Lou J, Ried R and Murphy, L J. Dexamethasone increases hepatic insulin-like growth factor-binding protein-1 (IGFBP-1) mRNA and serum IGFBP-1 concentrations in the rat. Endocrinology 1990; 127: 1456–1462.

McCarthy T L, Centrella M and Canalis E. Cortisol inhibits the synthesis of insulin like growth factor-I in skeletal cells. Endocrinology 1990; 126: 1569–1575.

Miell J P, Taylor A M, Jones J. Holly J M P, Gaillard R C, Pralong F P, Ross R J M and Blum W F. The effects of dexamethasone treatment on immunoreactive and bioactive insulin-like growth factors (IGFs) and IGF-binding proteins in normal male volunteers. J Endocrinol 1993; 136: 525–533.

Shimizu K, Amagaya S and Ogihara Y. Analysis of corticosterone in the serum of mice and rats, using high performance liquid chromatography. J. Chromatogr 1983; 272: 170–175.

Sapir D G, Pozefsky T, Knochel J P and Walser M. The role of alanine and glutamine in steroid-induced nitrogen wasting in man. Clin Sci Mol Med 1977; 53: 215–220.

SAS Institute Inc. SAS user's guide, statistics, 5th ed. SAS Institute Inc., Cary, N.C. 1985.

Simmons P S, Miles J M, Gerich J E and Haymond M W. Increased Proteolysis: An effect of increases in plasma cortisol within the physiological range. J Clin Invest 1984; 73: 412–420.

Skottner A, Clark R G, Fryklund L and Robinson I C A F. Growth responses in a mutant dwarf rat to human growth hormone and recombinant human insulin-like growth factor I. Endocrinology 1989; 124: 2519–2526.

Smith R and Williamson D H. Biochemical effects of human injury. Trends Biochem Sci 1983; 8: 142–146.

Tomas F M, Knowels S E, Owens P C, Chandler C S, Francis G L, Read L C and Ballard F J Insulin-like growth factor-I (IGF-I) and especially IGF-I variants are anabolic in dexamethasone-treated rats. Biochem J 1992; 282: 91–97.

Trainer P J, Kirk J M W, Savage M O, Grossman A B and Besser G M. Pyridostigmine partially reverses dexamethasone-induced inhibition of the growth hormone response to growth hormone-releasing hormone: J Endocrinol 1992; 134: 513–517.

Woolfson A M J, Heatley R V and Allison S P. Insulin to inhibit protein catabolism after injury. N Engl J Med 1979; 300: 14–17.

Örtoft G, Kelly C, Brüel A-M, Smith A, Carter N and Oxlund H. Glucocorticoids inhibit the growth hormone induced increase in serum IGF-I and its mRNA, body weight and muscle mass of rats. Eur J Exp Musculoskel Res 1993; 2: 135–142.

We claim:

1. A method for counteracting a decrease in nitrogen balance and counteracting a decrease in protein synthesis in an individual, comprising administering to the individual a combination of insulin and IGF-I, wherein IGF-I is administered in an amount to counteract a decrease in nitrogen balance and insulin is administered in an amount sufficient to potentiate the anticatabolic effect of IGF-I.

2. A method according to claim 1 for treatment of protein catabolism due to glucocortoid excess in an individual, comprising administering to the individual the combination of insulin and IGF-I.

3. A method according to claim 1 wherein the combination is administered to an individual with cardiac disease.

4. A method according to claim 1, wherein the combination contains IGF-I and insulin in a ratio of 30:1 to 2:1, based on molecular weight.

5. A method according to claim 4, wherein the combination contains IGF-I and insulin in a ratio of less than 10:1, based on molecular weight.

6. A method according to claim 5, wherein the combination contains IGF-I and insulin in a ratio of less than 8:1, based on molecular weight.

7. A method according to claim 1, wherein IGF-I is administered in a dose of 20 to 500 microgram/kg and insulin is administered in a dose of 10 to 100 microgram/kg.

8. A method according to claim 1, wherein the combination is administered to an individual having high serum level of IGFBP1.

9. A method according to claim 1, wherein the combination is administered to an individual having high serum level of low molecular weight BP.

10. A method according to claim 1, wherein the combination is administered to an individual which is insulin-resistant or which has liver disease.

11. A method for counteracting a decrease in nitrogen balance and counteracting a decrease in protein synthesis in an individual, comprising administering to the individual a combination of IGF-1 and insulin, wherein said insulin is in an amount sufficient to potentiate a synergistic effect of the anticatabolic effect of IGF-1.

12. A method according to claim 11 for treatment of protein catabolism due to glucocortoid excess in an individual, comprising administering to the individual the combination of insulin and IGF-I.

13. A method according to claim 11 wherein the combination is administered to an individual with cardiac disease.

14. A method according to claim 11, wherein the combination contains IGF-I and insulin in a ratio of 30:1 to 2:1, based on molecular weight.

15. A method according to claim 14, wherein the combination contains IGF-I and insulin in a ratio of less than 10:1, based on molecular weight.

16. A method according to claim 15, wherein the combination contains IGF-I and insulin in a ratio of less than 8:1, based on molecular weight.

17. A method according to claim 11, wherein IGF-I is administered in a dose of 20 to 500 microgram/kg and insulin is administered in a dose of 10 to 100 microgram/kg.

18. A method according to claim 11, wherein the combination is administered to an individual having high serum level of IGFBP1.

19. A method according to claim 11, wherein the combination is administered to an individual having high serum level of low molecular weight BP.

20. A method according to claim 11, wherein the combination is administered to an individual which is insulin-resistant or which has liver disease.

* * * * *